US008127626B2

(12) United States Patent
Hayes

(10) Patent No.: US 8,127,626 B2
(45) Date of Patent: Mar. 6, 2012

(54) SEDIMENT SAMPLER FOR IN-SITU MEASUREMENT OF SOLUBLE CONTAMINANT FLUX RATES

(75) Inventor: Thomas David Hayes, Schaumburg, IL (US)

(73) Assignee: Gas Technology Institute, Des Plaines, IL (US)

( * ) Notice: Subject to any disclaimer, the term of this patent is extended or adjusted under 35 U.S.C. 154(b) by 355 days.

(21) Appl. No.: 12/627,220

(22) Filed: Nov. 30, 2009

(65) Prior Publication Data

US 2011/0126644 A1    Jun. 2, 2011

(51) Int. Cl.
*G01N 1/10* (2006.01)
(52) U.S. Cl. .................................. 73/863.25
(58) Field of Classification Search ............... 73/863.23, 73/863.25, 864.91
See application file for complete search history.

(56) References Cited

U.S. PATENT DOCUMENTS

| | | | | |
|---|---|---|---|---|
| 5,140,845 | A * | 8/1992 | Robbins ....................... | 73/19.03 |
| 5,804,743 | A * | 9/1998 | Vroblesky et al. ........... | 73/863.23 |
| 5,942,440 | A * | 8/1999 | Dooley et al. ................ | 436/146 |
| 7,311,011 | B2 * | 12/2007 | Clark et al. .................. | 73/864.74 |
| 7,334,486 | B1 * | 2/2008 | Klammler et al. ........... | 73/861.07 |
| 7,896,578 | B2 * | 3/2011 | Keller .......................... | 405/150.1 |
| 8,069,715 | B2 * | 12/2011 | Keller .......................... | 73/152.28 |
| 2005/0235757 | A1 * | 10/2005 | De Jonge et al. ............ | 73/861.07 |
| 2009/0038390 | A1 * | 2/2009 | Dahan ........................... | 73/152.24 |

OTHER PUBLICATIONS

Cherkauer et al., "A Remotely Operated Seepage Meter for Use in Large Lakes and Rivers," Mar. 1988, Ground Water, vol. 26, No. 2, pp. 165-171.*

Chadwick et al., "Monitoring of Water and Contaminant Migration at the Groundwater-Surface Water Interface, Final Cost and Performance Report," Jan. 2008, ER200422, SSC San Diego, Technical Report 1966, pp. 9-217.*
Usepa, "Sampling for Contaminants in Sediments and Sediment Pore Water", Measurement and Monitoring Technologies for the 21st Century, Technology Innovation Program, http://clu-in.org/programs/21m2/sediment, pp. 1-19, (2004).
Nayar, S. et al., "A simple, inexpensive and large volume pore water sampler for sandy and muddy substrates", Estuarine, Coastal and Shelf Science, 66: 298-302 (2006).
Committee on Bioavailability of Contaminants in Soils and Sediments, National Research Council, "Bioavailability of Contaminants in Soils and Sediments: Processes, Tools and Applications", National Academies Press, Washington, D.C., pp. 216-231 (2003).
RMP Sediment Work Group, "Recommendation for Improvement of RMP Sediment Monitoring", San Francisco Estuary Institute, Richmond, CA (1999).
Hayes, T.D. et al., "Vapor pressure characterization to predict contaminant releases from MGP site source area soils", Soil and Sediment Contamination, 15(5):511-527 (2006).
Linz, David G. et al., Environmentally Acceptable Endpoints in Soil, American Academy of Environmental Engineers, pp. 35-40 (1997).

* cited by examiner

*Primary Examiner* — John Fitzgerald
(74) *Attorney, Agent, or Firm* — Mark E. Fejer

(57) ABSTRACT

A method and apparatus for in-situ measurement of soluble contaminant flux rates from sediments in which an inverted desorption chamber containing a sorbent system is filled with water and placed over an area of sediment, whereby the interior of the chamber is isolated from the exterior of the chamber above the sediment. Soluble contaminants released from the sediment are sorbed onto the surface of a sorbent material disposed within a plurality of semipermeable membrane bags disposed within the chamber. Each semipermeable membrane bag is removed from the chamber in a predefined sequence over a period of time and the sorbent material in each bag is analyzed to determine an amount of the soluble contaminant sorbed by the sorbent material. From the results of the analyses, the mass of the soluble contaminant removed from the sediment over time can be calculated.

17 Claims, 6 Drawing Sheets

SEDIMENT SAMPLER FOR IN-SITU MEASUREMENT OF SOLUBLE CONTAMINANT FLUX RATES

BACKGROUND OF THE INVENTION

This invention relates to a method and apparatus for measuring in-situ the flux rates of soluble contaminants in sediments.

One of the most costly environmental management challenges facing the United States and other modern countries is the monitoring and management of sediments that have been contaminated through industrial activity. Contaminants of concern include both organic pollutants and heavy metals that have been released to sediments and strata underlying sediments of various water bodies including rivers, streams, wetlands, estuaries, lakes, etc. (Linz, D. G. et al., *Environmentally Acceptable Endpoints in Soil*, American Academy of Environmental Engineers, pp. 35-40., 1997). Management options include long term monitoring, in-situ (in-place) remediation using treatment technologies, removal and disposal, and installation of a "cap" consisting of a stratum or combination of strata (such as bentonite or bauxite) that offer passive or active resistance to the transport of contaminants to the overlying water column.

One of the most difficult problems is the empirical measurement of contaminant flux rates occurring in the actual environment. Current methods of estimating flux rates involve the removal of sediment material from the environment and the placement of this material into artificial test systems usually consisting of microcosms or columns operated in the laboratory Committee on Bioavailability of Contaminants in Soils and Sediments, National Research Council, "Bioavailability of Contaminants in Soils and Sediments: Processes, Tools and Applications", National Academies Press, Washington, D.C., pp. 216-231 (2003); Linz, D. G. et al., *Environmentally Acceptable Endpoints in Soil*, American Academy of Environmental Engineers, pp. 35-40, 1997). The disadvantage of this approach is that the structure of the strata and the physical distribution of contaminants can be disrupted, making the laboratory apparatus non-representative of the actual transport regime of the existing sediment/capping system.

One method currently employed for measuring the flux rates of contaminants in sediments consists of the collection of grab samples using conventional equipment (see USEPA, "Sampling for Contaminants in Sediments and Sediment Pore Water", Measurement and Monitoring Technologies for the 21st Century, Technology Innovation Program., http://clu-in.org/programs/21m2/sediment, pp. 1-19, (2004)) and placing the sediment in laboratory microcosms (i.e. bench scale columns or aquaria) where volumes of water can be passed through the sediment material to measure contaminant mobility. Large volumes of water are sometimes collected from these laboratory units if contaminants are of low solubility. These large volumes of water are extracted into small volumes of extractant (e.g. solvent) for purposes of concentrating contaminants to measurable levels. However, these laboratory units do not simulate the actual aquatic environment, as a result of which sediments that are collected and charged into laboratory units are disturbed and do not represent contaminant transport characteristics of the undisturbed in-situ sediment environment. In closed laboratory units, the bulk water above the sediments contains levels of contaminants approaching equilibrium with the sediment solids. In the normal aquatic environment, the bulk water provides a high dilution of the contaminant released from the sediment. Thus, the driving gradients for transport of contaminants in the natural environment are higher than observed in laboratory units unless the laboratory units are continually flushed with fresh water. In addition, laboratory microcosms that are continually flushed with water are expensive to operate and analytical data from these systems is difficult to translate into an estimate of cumulative flux through the surface of the sediment over time to calculate flux rates.

SUMMARY OF THE INVENTION

It is one object of this invention to provide a method and apparatus for determining the flux rates of soluble contaminants in sediments which addresses the disadvantages of conventional methods and apparatuses.

It is one object of this invention to provide a method and apparatus for measuring in-situ the flux rates of soluble contaminants in sediments.

It is one object of this invention to provide a method and apparatus for measuring in-situ the flux rates of soluble contaminants in sediments which permits desorption of the contaminants from the surface of undisturbed strata to the bulk water overlying the sediment.

These and other objects of this invention are addressed by an apparatus for in-situ measurement of soluble contaminant flux rates in sediments comprising an open bottom chamber having at least one side wall, and having a top wall closing off the top of the chamber and forming a plurality of openings. A sorbent system comprising a plurality of removable porous enclosures, each containing a semipermeable membrane bag containing an ion exchange resin or a contaminant sorbent suitable for sorbing at least one soluble contaminant is disposed within the chamber. The porous enclosures in which the soluble contaminants are collected are sized to pass through the openings in the top, thereby enabling ready removal of the enclosures for analysis. Removable sealing means provided for sealing each of the openings in the top are connected with each of the porous enclosures, resulting in the formation of a seal between the porous enclosure and the perimeter of the opening, thereby precluding the escape of fluid which may be present from within the chamber or the intake of fluid from outside the chamber. Removal means are provided for individually removing each of the porous enclosures, and close-off means are provided for closing off the openings upon removal of corresponding porous enclosures from within the chamber.

In operation, the chamber having an open bottom, at least one side wall, and a top wall closing off the top of the chamber is filled with water and placed over an area of sediment, whereby the interior of the chamber is isolated from the exterior of the chamber above the sediment. Soluble contaminants released from the sediment are sorbed onto the surface of a sorbent material disposed within a plurality of semipermeable membrane bags disposed within the chamber. Each semipermeable membrane bag is removed from the chamber in a pre-defined sequence over a period of time and the sorbent material in each bag is analyzed to determine an amount of the soluble contaminant sorbed by the sorbent material. From the results of the analyses, the mass of the soluble contaminant removed from the sediment over time can be calculated.

BRIEF DESCRIPTION OF THE DRAWINGS

These and other objects and features of this invention will be better understood from the following detailed description taken in conjunction with the drawings, wherein.

DETAILED DESCRIPTION OF THE PRESENTLY PREFERRED EMBODIMENTS

Figure 1:
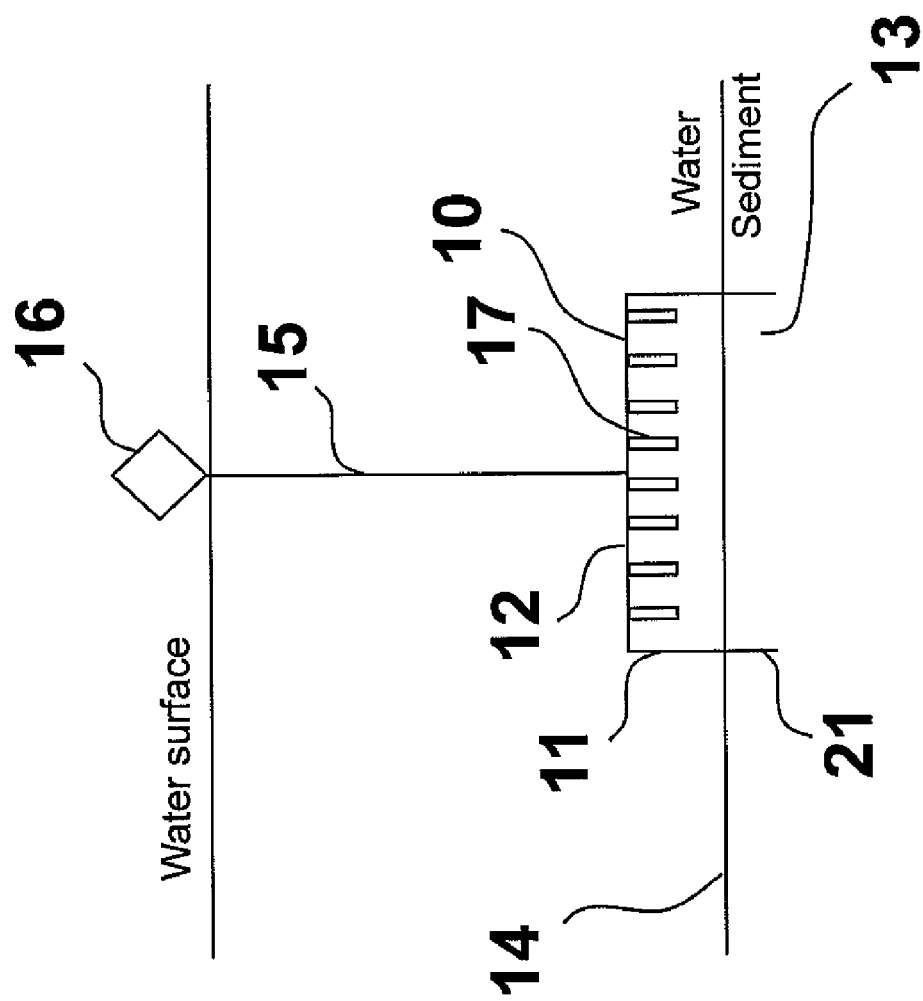
FIG. 1 is a schematic diagram showing the basic components of a sediment desorption sampling apparatus in accordance with one embodiment of this invention applied to a body of water.
Figure 2:
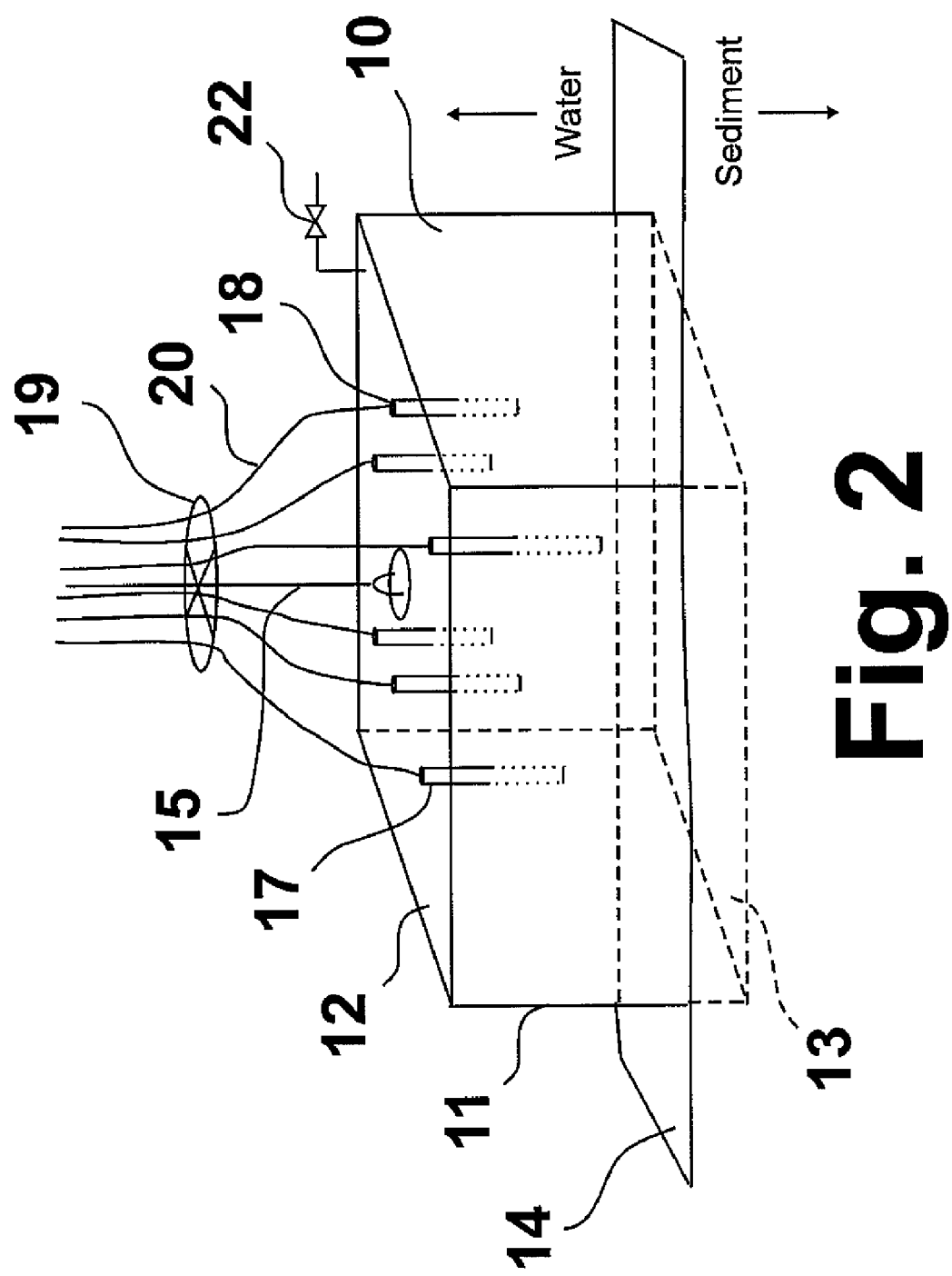
FIG. 2 is a schematic diagram of a sediment desorption sampling apparatus in accordance with one embodiment of this invention.

The invention disclosed herein, as shown in FIGS. 1 and 2, comprises a desorption chamber 10 having at least one side wall 11, a top wall 12 closing off the top of the chamber, and an open bottom 13 that is positioned over a defined area of sediment 14. The desorption chamber is connected with one end of a line or cable 15, the other end of which is connected with a buoy 16 on the water surface. The bottom edge 21 of the at least one side wall 11 is a knife edge for facilitating placement of the desorption chamber in and above the sediment. A sorbent system designed to measure the transport of soluble contaminants released from the sediment surface is disposed within the desorption chamber.

Figure 3:
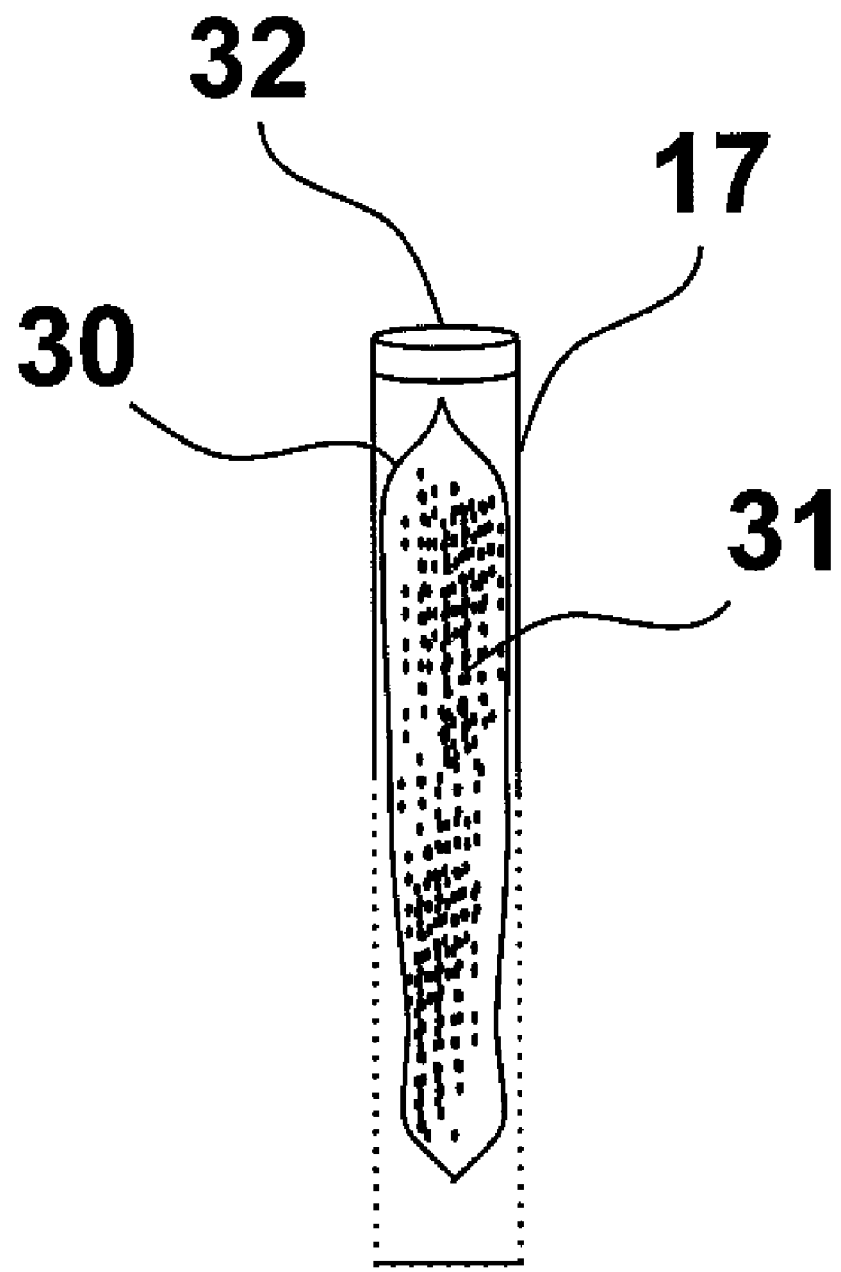
FIG. 3 is a schematic diagram of a porous enclosure of a sediment desorption sampling apparatus in accordance with one embodiment of this invention.

The sorbent system comprises a plurality of porous enclosures 17 disposed within the desorption chamber 10 which are individually removable from the desorption chamber. Each porous enclosure has a closed-off top side or end 32 and contains a semipermeable membrane bag 30 containing an ion exchange resin or a contaminant sorbent 31 suitable for sorbing at least one soluble contaminant being released from the sediment as shown in FIG. 3. To enable removal of the porous enclosures from within the desorption chamber, the top wall 12 forms a plurality of openings 18 sized to accommodate passage of the porous enclosures through the top wall. The number of openings in the top wall corresponds to the number of porous enclosures initially within the desorption chamber. Connected with each porous enclosure are removal means for individually removing the porous enclosures from within the desorption chamber. In accordance with one preferred embodiment, such removal means comprises a harness 19 controlling a plurality of cables 20 connected at one end in a one-to-one relationship with the porous enclosures. The other end of each cable extends above the surface of the water in which the apparatus is submerged, thereby enabling removal of the porous enclosures from the desorption chamber one at a time. It will be appreciated that other means for individually removing the porous enclosures from within the desorption chamber, such as a rod connected with each porous enclosure, may be employed and such other means are deemed to be within the scope of this invention.

Figure 4:
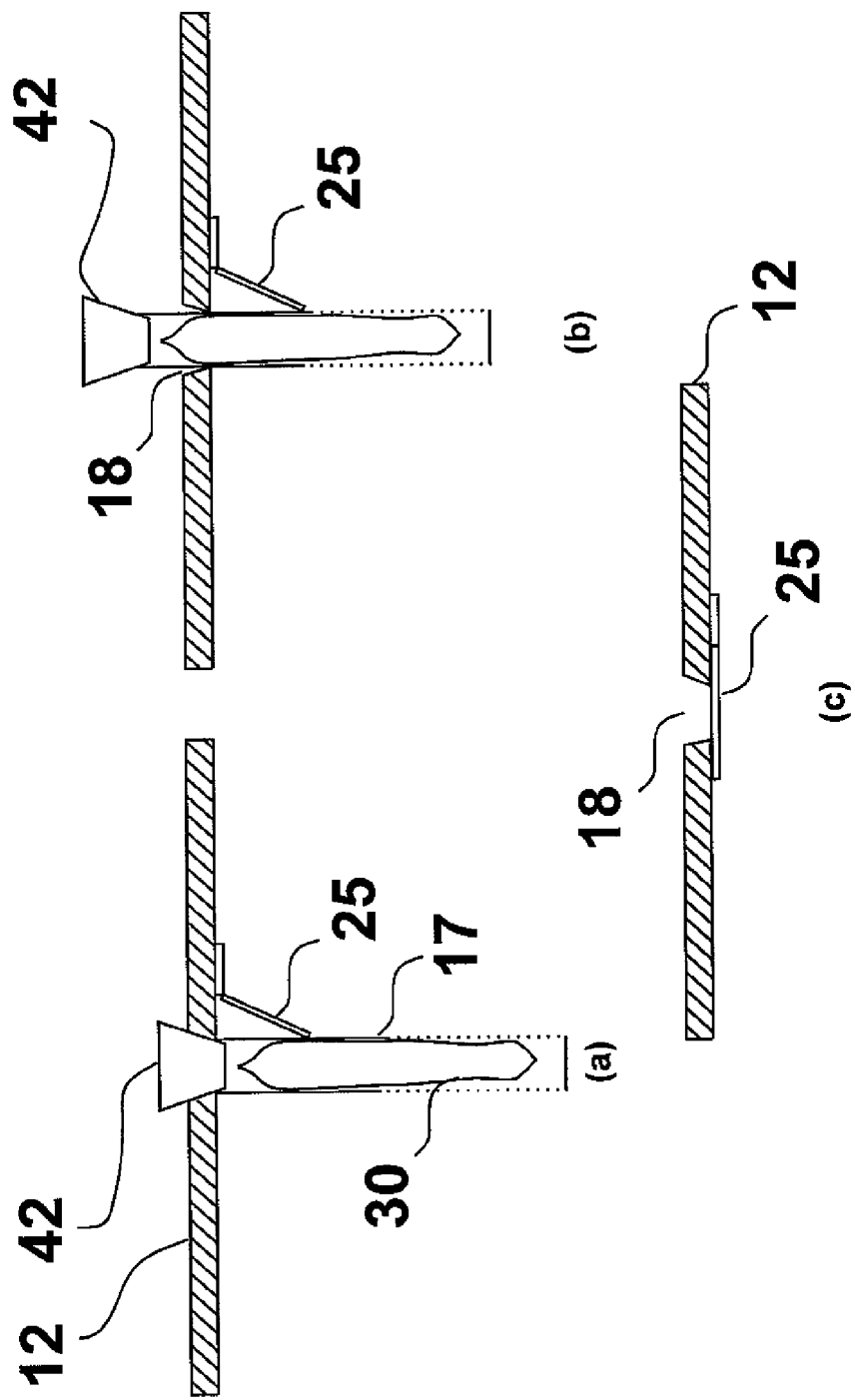
FIG. 4 is a partial cross-sectional diagram showing removal of a porous enclosure from within the chamber of the sediment desorption sampling apparatus in accordance with one embodiment of this invention.
Figure 5:
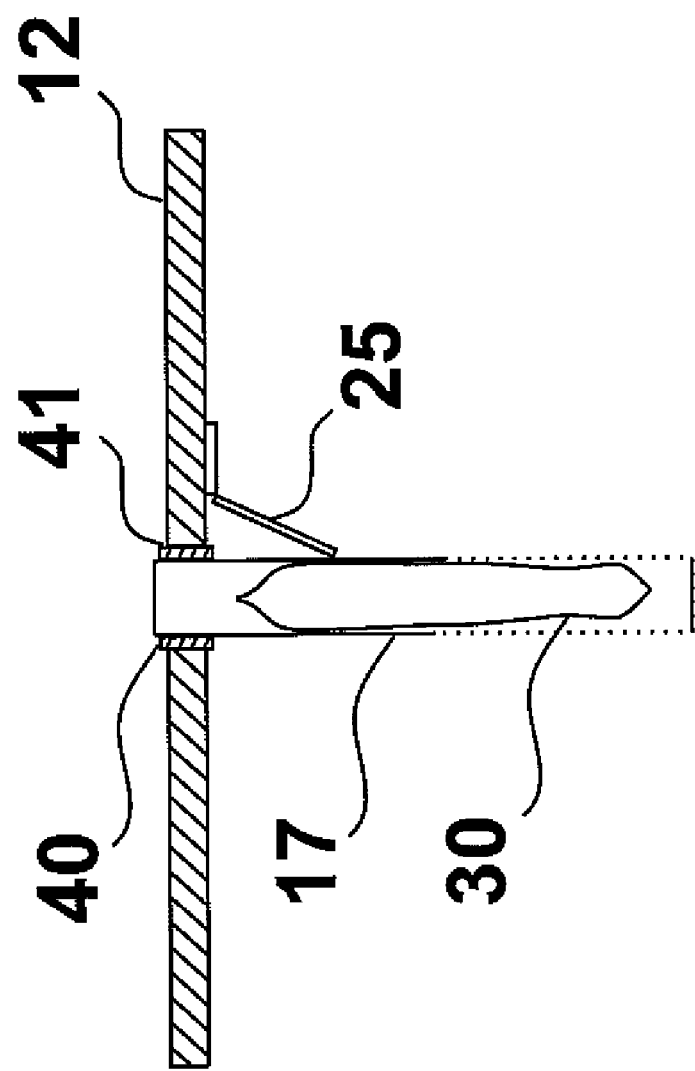
FIG. 5 is a partial cross-sectional diagram showing sealing means for sealing each opening for removal of each porous enclosure in accordance with one embodiment of this invention.

One of the requirements of the method and apparatus of this invention is that the interior space of the desorption chamber above the sediment surface be completely isolated from the environment exterior to the chamber. In this regard, it will be appreciated that with a portion of the chamber deeply embedded within the sediment, the intake of water in the environment surrounding the chamber above the surface of the sediment through the open bottom of the chamber is precluded. Accordingly, disposition of the porous enclosures within the chamber and removal of the porous enclosures from the chamber must necessarily be accomplished in a manner which precludes either the escape of water from inside the chamber or the intake of water from the surrounding environment into the interior of the chamber. In accordance with one embodiment of this invention, a compressible sleeve 40 is disposed around each porous enclosure 17 so as to provide a seal between the perimeter 41 of each opening 18 formed by the top wall 12 of the desorption chamber 10 and the corresponding porous enclosure (FIG. 5). In accordance with another embodiment, the seal is formed by a stopper 42 as shown in FIG. 4. In order to prevent fluid exchange between the environment surrounding the desorption chamber and the water within the chamber during removal of the porous enclosures, a spring-loaded trap door 25 sized to cover the area of a corresponding opening is connected with the underside of the top wall as shown in FIG. 4. As a result, upon removal of a porous enclosure through a corresponding opening, the spring-loaded trap door closes to cover the opening and prevent any substantial fluid exchange ((a), (b), (c) in FIG. 4).

During the initial placement of the desorption chamber within the sediment, air may be trapped in the chamber. To enable removal of the trapped air, a valve 22 having an inlet in fluid communication with the interior of the chamber is connected with the chamber. The valve is opened to remove any trapped air and upon removal of all the trapped air the valve is closed.

The invention in accordance with one preferred embodiment comprises an inverted, stainless steel desorption chamber that is positioned over a defined area of sediments (for example, 1 square meter), outfitted with a sorbent system designed to measure the transport of soluble contaminants released from the sediment surface. The desorption chamber is flooded with water and contains no air pockets. The chamber is equipped with five to ten porous stainless steel tubes inserted in separate holes positioned on the top surface of the box. Considerable flexibility can be exercised in the design of the pores within the removable tubes. Pores of each tube should be at least 2 mm in width and the pore area to total tube side area should greater than 0.1. In addition, the bottom end of the porous tube may be open or, preferably, closed off. Each of these porous steel tubes contains a semipermeable membrane bag filled with 3-20 grams of sorbent media (such as activate carbon or molecular sieve material) or ion exchange resin. The membrane bag holding the sorbent material is comprised of a semipermeable material (such as dialysis tubing from Sigma Corporation) with a molecular weight cut-off of 5,000 to 200,000 daltons. Each sorbent bag is placed inside a stainless steel tube that is inserted into the inner contents of the chamber. The porous stainless steel tubes are positioned in a manner that allows the membrane bags to be exposed to the water of the chamber which is in contact with the sediments. Each steel tube is also positioned through a rubber sleeve or stopper in the top of the desorption chamber (as shown in FIG. 4) in a manner where the tube is sealed to the surface of the box and where the water within the chamber is not in communication with the water outside the chamber. The type of sorbent medium used is determined on the basis of the ability of the sorb ent medium to remove the sought after contaminant from the sediment. An approximation of the total amount of sorptive media required to charge the tubes can be calculated from an upper-end estimate of the total contaminant(s) that are released and adsorbed over the time that the device is placed over the sediment.

Although described herein as being constructed of stainless steel, the apparatus of this invention may be constructed from other inert materials that are of sufficient strength and that are non-adsorbent and non-reactive with chemicals of concern and which are not likely to break apart during use in the field. Examples of alternate materials include teflon coated steel, nalgene, polycarbonate, and monel.

Figure 6:
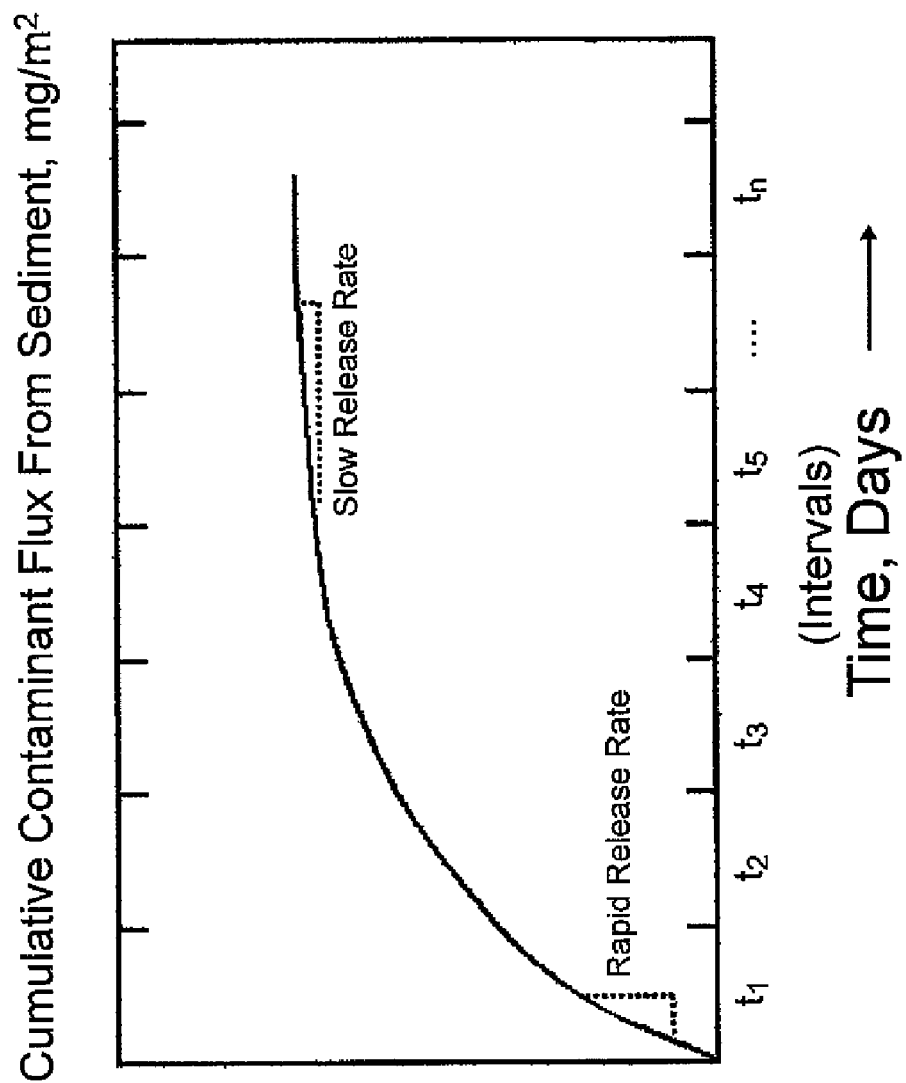
FIG. 6 is a diagram showing cumulative contaminant flux through sediment versus time.

In operation, the stainless steel desorption chamber, flooded with the water, is lowered to the sediment floor of the water body. The knife edges of the side walls along the open face of the chamber allow the edges of the chamber to be inserted several centimeters into the sediment. The water within the flooded metal chamber is in contact with the sediments, but sealed with respect to contact with the water outside the chamber. During the sampling period, sought-after soluble contaminants released from the sediments into the water matrix of the chamber are transported through the semipermeable membrane bag of all of the porous stainless steel tubes and are sorbed to the surface of the sorbent material. In this time period, the concentration of soluble contaminant in the water phase of the chamber is approximately zero, a condition that provides a maximum driving gradient in the transport of contaminant from the sediment solids to the water phase. Over a defined sampling period, each individual tube is removed and recovered in a certain time sequence and the sorptive medium is analyzed for the sought-after contaminant(s). The tubes are removed and brought to the surface through individual cables. As the tubes are removed from their respective openings or holes in the desorption chamber, a spring-loaded flap is actuated to close the hole and keep the chamber sealed off from the outside water. Equations based on conservative materials balances are used to calculate the mass of soluble contaminant removed from the sediment with time. Mathematical expressions used to calculate flux rate and cumulative flux for each time interval are shown in Table 1. The data and calculations allow cumulative flux to be plotted with time for the sediment. As shown in FIG. 6, this plot can be used to determine the rapid and slow release rates of a contaminant from the sediment with time.

Thus, the unique features of this invention include: 1) the establishment of a sealed chamber that is placed over a specific area of sediment that does not allow for communication of the bulk water outside the chamber with the water volume that is inside the chamber; 2) the use of a semipermeable membrane bag to contain the sorbent material and to ensure that only the soluble fraction of the contaminant is removed from the aqueous phase as distinguished from the insoluble forms of the contaminant (i.e. contaminant sorbed to sediment particulates, insoluble precipitates, colloids, etc.); 3) the establishment of an aqueous environment within the chamber where the concentration of soluble contaminant is zero due to the adsorption of contaminant to the sorbent within the stainless steel sorption tubes; 4) the establishment of a maximum gradient for the desorption of soluble contaminant from the sediment surface (due to the reduced soluble contaminant concentration in the water phase of the chamber); and 5) the ability to measure the transport of contaminant from the sediment to the water phase with time through the sequential collection and analysis of the stainless steel tubes. These features constitute a sediment sampler that has the capability to provide a conservative upper-end estimate of the flux of contaminants with time from sediment materials.

Advantages of the invention over conventional samplers are as follows: a) contaminant release is measured in the real ("in-situ") environment, not in disturbed sediment samples collected as "grab samples" or as cores that are taken to an artificial lab environment for measurements of contaminant release; b) contaminant flux measurements yield upper-end, conservative estimates of release rates; c) the sampler is applicable to the in-situ, mobility measurement of a wide range of organic contaminants when certain sorbents are used such as activate carbon and synthetic resins (such as XAD and Ambersorb sorbents manufactured by Rohm & Haas). Examples of organic contaminants that can be measured by the invention include but are not limited to aromatic compounds (BTEX, PAH's, etc.), chlorinated hydrocarbons (PCB's, solvents, etc.), pesticides, munitions, etc.; d) the sampler is applicable to the in-situ mobility measurement of heavy metals and anionic contaminant species when ion exchange media is used as the sorbent material within the semipermeable membrane bags; e) the sampler can provide

TABLE 1

Mathematical Expressions Relating the Mass of Contaminant Measured on Each Sorbent Tube ($M_n$) Sequentially Removed After Each Sample Interval ($t_n$) to the Calculation of Flux Rate and Cumulative Flux.

| Sample Interval | Cumulative Mass of Contaminant Captured on Sorbent* | Mass Capture on Sorbent During the Interval $t_n$ | Total Mass Mobilized to Sorbent During Interval $t_n$ | Flux Rate $Kg/m^2$-d | Cumulative Flux (Release) from Sediment by the End of Each Interval, $Kg/m^2$ |
|---|---|---|---|---|---|
| $t_1$ | $M_1$ | $M_1$ | $nM_1$ | $nM_1/(A\,t_1)$ | $nM_1/A$ |
| $t_2$ | $M_2$ | $M_2 - M_1$ | $(n-1)(M_2 - M_1)$ | $(n-1)(M_2 - M_1)/(A\,t_2)$ | $(M_1 + (n-1)M_2)/A$ |
| $t_3$ | $M_3$ | $M_3 - M_2$ | $(n-2)(M_3 - M_2)$ | $(n-2)(M_3 - M_2)/(A\,t_3)$ | $(M_1 + M_2 + (n-2)M_3)/A$ |
| $t_4$ | $M_4$ | $M_4 - M_3$ | $(n-3)(M_4 - M_3)$ | $(n-3)(M_4 - M_3)/(A\,t_4)$ | $(M_1 + M_2 + M_3 + (n-3)M_4)/A$ |
| $t_5$ | $M_5$ | $M_5 - M_4$ | $(n-4)(M_5 - M_4)$ | $(n-4)(M_5 - M_4)/(A\,t_5)$ | $(M_1 + M_2 + M_3 + M_4 + (n-4)M_5)/A$ |
| $t_6$ | $M_6$ | $M_6 - M_5$ | $(n-5)(M_6 - M_5)$ | $(n-5)(M_6 - M_5)/(A\,t_6)$ | $(M_1 + M_2 + M_3 + M_4 + M_5 + (n-5)M_6)/A$ |
| $t_n$ | $M_n$ | $M_n - M_{n-1}$ | $(n-(n-1))(M_n - M_{n-1})$ | $(n-(n-1))(M_n - M_{n-1})/(A\,t_n)$ | $(M_1 + M_2 + M_3 + M_4 + M_5 + M_6 + \ldots + M_n)/A =$ Total Mass desorbed from the sediments with sorbent materials |

*$M_n$ = Mass of the contaminant measured on the content of each sequentially removed Sorbent Tube using vendor recommended procedures for extraction and standard USEPA methods for contaminant analysis.

the simultaneous, in-situ, mobility measurement of the desorption of multiple contaminants from the sediments when mixtures of sorbent materials are placed in each semipermeable membrane bag or when each of the stainless steel tubes contains two or more different types of semipermeable membrane bags (in either case, each stainless steel tube contains the same type of materials); f) the sampler measures the mobility of soluble constituents from the sediment interface. The release rate data that can be obtained for the in-situ system can be used to estimate the concentrations of contaminant in the pore water environment of the sediment, replacing more expensive conventional methods of pore water measurement that involve physical withdrawals of large amounts of pore water from sediment strata and extracting these large volumes of water with solvents for subsequent analysis for estimation of the mobile fraction; g) the sampler is potentially capable of measuring the fast and slow release fractions of contaminants through the forced desorption of the contaminants from the sediments; and h) the invention is comprised of low-cost materials that allow the device to be applied to monitoring wide areas at relatively low expense. Compared with conventional pore water analysis to measure contaminant mobility, the invention is able to provide a far better measurement representing the undisturbed sediment at a cost reduction of more than 80 percent in most cases.

The device may also be used to measure the contaminant flux rates before and after remedial measures (such as chemical oxidation, biological treatment, capping, etc.) designed to mitigate contaminant release from sediments, thus providing empirical evidence of the efficacy of these methods.

EXAMPLE 1

Organic Contaminant Measurements

Runoff from upstream oil and gas production and gas liquids treatment plants into streams has raised questions over whether the sediments of the water body need to be dredged and treated. Contaminants of greatest concern include benzene, toluene and xylenes. On the basis of sediment sampling literature, it appears that concentrations of organics in the upper 10 cm are of high interest when estimating transport flux from the sediment USEPA, "Sampling for Contaminants in Sediments and Sediment Pore Water", Measurement and Monitoring Technologies for the 21st Century, Technology Innovation Program, http://clu-in.org/programs/21m2/sediment, pp. 1-19, (2004); Nayar, S., D. et al., "A simple, inexpensive and large volume pore water sampler for sandy and muddy substrates", Estuarine, Coastal and Shelf Science 66: 298-302, 2006.; RMP Sediment Work Group, "Recommendation for Improvement of RMP Sediment Monitoring", San Francisco Estuary Institute, Richmond, Calif. 1999). Data from grab samples previously taken of the sediments suggest BTEX (benzene, toluene, ethylbenzene and xylenes) concentrations in the upper 10 cm range from <5 ppb to 2,100 ppb. Assuming that a desorption chamber of 1 m$^2$ is to be used for sampling, it is calculated that approximately 170 kg of sediment is contained in the zone of interest down to a depth of 10 cm within the desorption chamber. Assuming the worst case that 2,100 ppb of contaminant is desorbed from the sediment during the sampling period, it is estimated that approximately 357 mg of contaminant will be transported from the sediment to the sorbent under the worse case. The sorbent selected is an adsorptive resin or charcoal with a sorption capacity of 5-15 percent. Assuming the worst case, the sorption capacity is 5 percent and it is estimated that the sorption of all of the contaminant released from the sediment will require 7.1 grams of resin (0.357/0.05=7.1). A safety factor of five is applied and a total sorbent requirement of 36 grams is estimated. Therefore, six stainless steel tubes are outfitted with sealed semipermeable membrane bags, each bag containing 6 grams of the sorbent resin, and the tubes are installed into the desorption chamber. At the aquatic site where sediments are to be characterized, the desorption chamber is lowered into the water while the air release valve is open. When all of the air is exhausted from the desorption chamber, the chamber is lowered to the sediments where the knife edges of the chamber settle several centimeters into the sediment. Once the chamber is set into the sediment, the top of the main cable is attached to a floating buoy for easy retrieval. At approximately day one, the first tube is removed using a retrieval cord. The other five tubes are pulled from the desorption chamber at designated intervals. Upon retrieval at the aquatic site, each of the stainless steel tubes is placed into a sealed sampling bottle for subsequent analysis. At the laboratory, all of the semipermeable membrane bags are opened and the sorptive resins are extracted and analyzed for the sought after contaminants using USEPA Method 8260B (SW-846). Using the equations of Table 1, the cumulative flux is plotted with time and the slow and rapid release rates are estimated. Flux rates are then computed.

EXAMPLE 2

Heavy Metal Release Measurements

In this example, lakeshore sediments contaminated with cadmium and copper are to be characterized for contaminant flux measurements. The desorption chamber is set up in a manner similar to Example 1 with the exception that cationic ion exchange media is used in the semipermeable membrane bags. Analysis of the sediments in the top 10 cm of sediment and an estimation technique similar to the method used in Example 1 leads to the calculation that about 60 grams of ion exchange media are needed in the desorption chamber. After the configured desorption chamber is set on top of the sediment, the stainless steel tubes are sequentially retrieved. Each of the ion exchange aliquots in the semipermeable membrane bags is extracted with a strong acid and analyzed for heavy metals using atomic absorption. Data from these analyses is used to plot contaminant flux with time from the sediment surface and calculate flux rates.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

What is claimed is:

1. An apparatus for in-situ measurement of soluble contaminant flux rates in sediments comprising:

a chamber having an open bottom, at least one side wall, and a top wall closing off a top of said chamber and forming a plurality of openings;

a sorbent system disposed within said chamber, said sorbent system comprising a plurality of removable porous enclosures, each said enclosure containing a semipermeable membrane bag containing one of an ion exchange resin and a contaminant sorbent suitable for sorbing at least one soluble contaminant, said porous enclosures sized to pass through said openings;

removable sealing means for sealing each said opening connected with each said porous enclosure;

removal means for individually removing each of said porous enclosures; and close-off means for closing off said openings upon removal of a corresponding said porous enclosure.

2. The apparatus of claim 1, wherein said removal means comprises a retrieval cord connected with each of said porous enclosures.

3. The apparatus of claim 1, wherein said at least one side wall comprises a knife edge around said open bottom.

4. The apparatus of claim 1, wherein said close-off means comprises a spring-loaded trap door element connected with an underside of said top wall and oriented to close off each said opening immediately upon removal of said corresponding porous enclosure.

5. The apparatus of claim 1 further comprising a valve connected with said top wall and having an inlet opening in fluid communication with an interior of said chamber.

6. The apparatus of claim 1, wherein said semipermeable membrane bag comprises a semipermeable material having a molecular weight cut-off in a range of about 5,000 daltons to about 200,000 daltons.

7. The apparatus of claim 1, wherein said removable porous enclosures are tubular elements having a closed off top end proximate said top wall and a bottom end distal from said top wall.

8. The apparatus of claim 7, wherein said removable sealing means comprises a compressible sleeve element disposed tightly around said top end of said tubular element and sized to fit tightly within said opening.

9. The apparatus of claim 7, wherein said removable sealing means comprises a stopper element closing off said top end of said tubular element and sized to fit tightly within said opening.

10. The apparatus of claim 7, wherein said bottom end of said tubular element is closed off.

11. A method for in-situ measurement of soluble contaminant flux rates in sediments comprising the steps of:

placing a water-filled chamber having an open bottom, at least one side wall, and a top wall closing off a top of said chamber over an area of sediment, whereby an interior of said chamber is isolated from an exterior of said chamber above said sediment;

sorbing a soluble contaminant released from said sediment to a surface of a sorbent material disposed within a plurality of semipermeable membrane bags, each said semipermeable membrane bag disposed within said chamber;

removing each said semipermeable membrane bag from said chamber in a pre-defined sequence over a period of time;

analyzing said sorbent material in each said semipermeable membrane bag to determine an amount of said soluble contaminant sorbed by said sorbent material; and calculating a mass of said soluble contaminant removed from said sediment over time.

12. The method of claim 11, wherein each of said semipermeable membrane bags is disposed in a porous enclosure.

13. The method of claim 12, wherein said semipermeable membrane bag comprises a semipermeable material having a molecular weight cut-off in a range of about 5,000 daltons to about 200,000 daltons.

14. The method of claim 12, wherein an aqueous environment is maintained within said chamber so as to maintain a concentration of said soluble contaminant of zero external to said porous enclosures.

15. The method of claim 12, wherein each of said porous enclosures is removed through a corresponding opening formed by said top wall following which said corresponding opening is automatically closed off.

16. The method of claim 15, wherein said porous enclosures are tubular elements having a closed off top end and a closed off bottom end.

17. The method of claim 16, wherein said top ends of said tubular elements are sealingly disposed within said corresponding openings, whereby said corresponding openings are sealed shut.

* * * * *